US012797410B2

(12) United States Patent
Simm et al.

(10) Patent No.: US 12,797,410 B2
(45) Date of Patent: Nov. 17, 2026

(54) REDUCTION OF ADVANCED GLYCATION ENDPRODUCTS FROM BODILY FLUIDS

(71) Applicant: CYTOSORBENTS CORPORATION, Princeton, NJ (US)

(72) Inventors: Andreas Viktor Simm, Salzatal OT Lieskau (DE); Jorg Scheier, Monmouth Junction, NJ (US); Christian Steiner, Monmouth Junction, NJ (US); Vincent Capponi, Monmouth Junction, NJ (US); Phillip P. Chan, Cherry Hill, NJ (US)

(73) Assignee: CytoSorbents Corporation, Princeton, NJ (US)

( * ) Notice: Subject to any disclaimer, the term of this patent is extended or adjusted under 35 U.S.C. 154(b) by 0 days.

(21) Appl. No.: 18/320,417

(22) Filed: May 19, 2023

(65) Prior Publication Data

US 2023/0310493 A1 Oct. 5, 2023

Related U.S. Application Data

(63) Continuation of application No. 16/638,834, filed as application No. PCT/US2018/048678 on Aug. 30, 2018, now abandoned.

(60) Provisional application No. 62/552,424, filed on Aug. 31, 2017.

(51) Int. Cl.
*A61K 31/79* (2006.01)
*A61K 31/717* (2006.01)
*A61K 31/78* (2006.01)

(52) U.S. Cl.
CPC ............ *A61K 31/79* (2013.01); *A61K 31/717* (2013.01); *A61K 31/78* (2013.01)

(58) Field of Classification Search
CPC ................ B01J 20/267; B01J 20/28078; B01J 20/28069; B01J 20/3208
See application file for complete search history.

(56) References Cited

U.S. PATENT DOCUMENTS 6,890,523 B2 5/2005 Bacon Kurtz et al.
2006/0078534 A1 4/2006 Charmot et al.
2009/0143226 A1* 6/2009 Inoue ........................ A61P 9/10 526/263
2011/0082421 A1 4/2011 Ameer et al.
2013/0072845 A1 3/2013 Tennison et al.
2013/0195792 A1 8/2013 Chan et al.
2013/0243785 A1 9/2013 Gruber
2015/0335576 A1* 11/2015 Chan .................... A61K 31/765 210/287
2016/0024233 A1 1/2016 Holmes-Farley et al.

FOREIGN PATENT DOCUMENTS

JP H07-275697 A 10/1995
JP H08-299788 A 11/1996
JP 2004-057536 A 2/2004
JP 2011-184403 A 9/2011
JP 2013-047175 A 3/2013
JP 2013-523772 A 6/2013
JP 2015-530969 A 10/2015
JP 2016-193882 A 11/2016
RU 2536232 C2 12/2014
WO WO 2007/037554 A1 4/2007
WO 2011123767 A1 10/2011

OTHER PUBLICATIONS

Twarda-Clapa et al (Cells, 2022, vol. 11, pp. 1-36) (Year: 2022).*
Zhang et al (Artificial Organs, 2014, vol. 38, pp. 474-483) (Year: 2014).*
Kandarakis et al (Progress in Retinal and Eye Research, 2014, vol. 42, pp. 85-102) (Year: 2014).*
Sasaki et al (The American Journal of Pathology, 1998, vol. 153, pp. 1149-1155) (Year: 1998).*
U.S. Appl. No. 16/638,834, filed Feb. 13, 2020.
International Patent Application No. PCT/US2018/048678; Int'l Search Report and the Written Opinion; dated Nov. 14, 2018; 14 pages.
International Patent Application No. PCT/US2018/048678; Int'l Preliminary Report on Patentability; dated Apr. 22, 2020; 8 pages.
European Patent Application No. 18852026.6; Extended Search Report; dated Jan. 18, 2021; 6 pages.
Kilhovd et al (Arteriosclerosis, Thrombosis, and Vascular Biology, 2005, vol. 25, pp. 815-820) (Year: 2005).
Ishibashi et al (Arch Ophthalmol, 1998, vol. 116, pp. 1629-1632) (Year: 1998).
Bidasee et al.; "Chronic Diabetes Increases Advanced Glycation End Products on Cardiac Ryanodine Receptors/Calcium-Release Channels"; Diabetes; vol. 52; Jul. 2003; p. 1825-1836.

* cited by examiner

*Primary Examiner* — Mark V Stevens
(74) *Attorney, Agent, or Firm* — BakerHostetler

(57) ABSTRACT

The invention concerns removing advanced glycation end products from a bodily fluid by contacting the bodily fluid with a sorbent.

17 Claims, 3 Drawing Sheets

REDUCTION OF ADVANCED GLYCATION ENDPRODUCTS FROM BODILY FLUIDS

CROSS REFERENCE TO RELATED APPLICATIONS

The present application is a continuation application of U.S. application Ser. No. 16/638,834, filed Feb. 13, 2020, which is a National Stage Application of International Patent Application No. PCT/US2018/048678, filed Aug. 30, 2018, which claims benefit of U.S. Patent Application No. 62/552,424, filed on Aug. 31, 2017, the disclosure of each of which is incorporated herein in its entirety.

TECHNICAL FIELD

The invention concerns reduction of advanced glycation end products from bodily fluids.

BACKGROUND

Degenerative diseases as well as aging are mainly based on a life-long accumulation of molecular damages within molecules, cells and tissues. Important examples of damaging structures are the advanced glycation end products (AGEs).

Advanced glycation end products (AGEs), pathophysiological important posttranslational modifications, are formed in vivo by a non-enzymatic reaction of proteins with reactive carbohydrates and accumulate during aging. They are discussed to be responsible for degenerative diseases. Glycation modifies the structure and function of proteins and induces tissue stiffening via crosslinking. Soluble AGEs can bind to receptors like the receptor for advanced glycation end products (RAGE). Binding to RAGE induces on the one hand the expression of RAGE itself and on the other hand, the expression of proinflammatory cytokines leading to a long-lasting inflammatory response. This may have an impact on aging, as aging is mostly connected to inflammation (Inflammaging). RAGE-knock out mice are protected in models of sepsis (increased survival). In the cardiovascular system, AGEs are a major cause of cardiac and vascular dysfunction.

High levels of AGEs have been linked with the development of a variety of diseases including diabetes, heart disease, kidney failure, Alzheimer's and macular degeneration. There is a need in the art for methods that treat, prevent or low the progression of diseases associated with AGEs.

SUMMARY

In some embodiments, the invention concerns method of removing advanced glycation end products from a bodily fluid comprising contacting the bodily fluid with a sorbent.

In certain embodiments, the invention concerns treatment of a degenerative disease by removing advanced glycation end products from a bodily fluid comprising contacting the bodily fluid with a sorbent

DETAILED DESCRIPTION OF ILLUSTRATIVE EMBODIMENTS

Figure 1A:
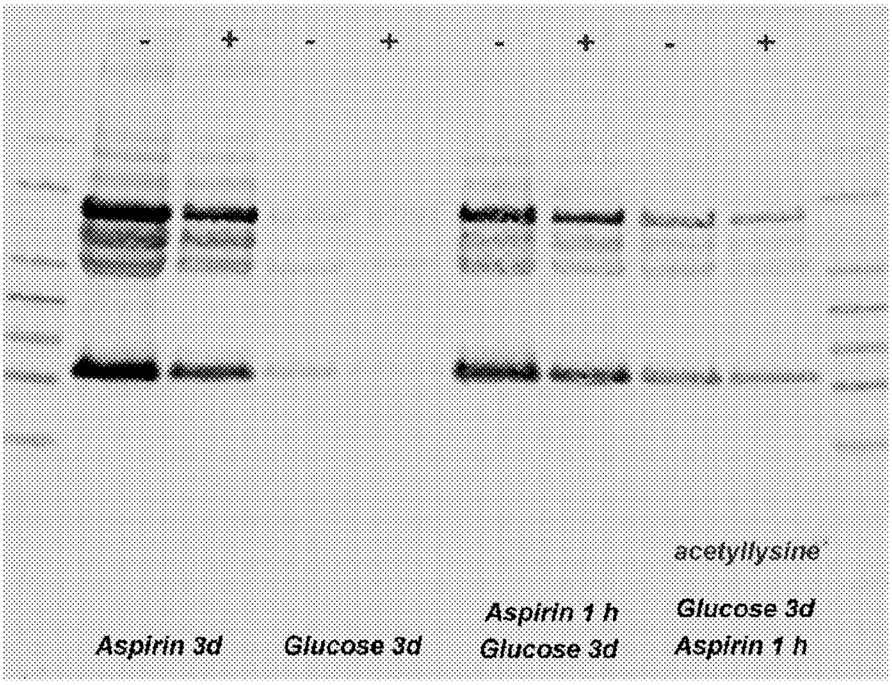
FIG. 1*a* shows that Cytosorbents Adsorber do not bind Acetyllysine efficiently.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges include each and every value within that range.

The term "biocompatible" is defined to mean the sorbent is capable of coming in contact with physiologic fluids, living tissues, or organisms without producing unacceptable clinical changes during the time that the sorbent is in contact with the physiologic fluids, living tissues, or organisms. In some embodiments, it is intended that the sorbent is tolerated by the gut and alimentary canal of the organism. The sorbents of the present invention are preferably non-toxic. A biocompatible sorbent may be a biodegradable polymer, a resorbable polymer, or both.

As used herein, the term "sorbent" includes adsorbents and absorbents.

As used herein, the term "physiologic fluids" are liquids that originate from the body and can include, but are not limited to, nasopharyngeal, oral, esophageal, gastric, pancreatic, hepatic, pleural, pericardial, peritoneal, intestinal, prostatic, seminal, vaginal secretions, as well as tears, saliva, lung or bronchial secretions, mucus, bile, blood, lymph, plasma, serum, synovial fluid, cerebrospinal fluid, urine, and interstitial, intracellular, and extracellular fluid, such as fluid that exudes from burns or wounds.

As used herein, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Unless defined otherwise, all other technical and scientific terms used herein have the same meaning as commonly understood by one of ordinary skill in the art pertinent to the methods and compositions described. As used herein, the following terms and phrases have the meanings ascribed to them unless specified otherwise.

The phrase "advanced glycation end products" represents proteins or lipids that become glycated. AGEs are harmful compounds that can be formed when protein or fat combine with sugar in the bloodstream in a process called glycation. AGEs can also be formed in foods, particularly foods exposed to high temperatures that can occur with grilling, frying or toasting, RAGE (receptor for advanced glycation end products) is a receptor that is able to bind advanced glycation end products. While not wanting to be bound by theory, it is believed that RAGE comprises a 35 kilodalton transmembrane receptor of the immunoglobulin super family.

Sorbents

In some embodiments, the sorbent comprises at least one crosslinking agent and at least one monomer. In other embodiments, the sorbent comprises at least one crosslinking agent, at least one monomer, at least one dispersing agent and at least one porogen.

Preferred sorbents comprise polymers derived from one or more monomers selected from divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

In certain embodiments, the sorbent is a biocompatible macroporous polymeric sorbent comprising residues of one or more monomers from the group comprising divinylbenzene and ethylvinylbezene, styrene, and ethylstyrene.

Some preferred polymers comprise ion exchange polymers.

Some preferred polymers comprise cellulosic polymers. Suitable polymers include cross-linked dextran gels such as Sephadex™.

Certain preferred polymers comprise porous highly cross-linked styrene or divinylbenzene copolymers. Some of these copolymers comprise a macroporous or mesoporous styrene-divinylbenzene-ethylstyrene copolymer subjected to a partial chloromethylation to a chlorine content of up to 7% molecular weight. Other of these polymers are a hypercrosslinked polystyrene produced from crosslinked styrene copolymers by an extensive chloromethylation and a subsequent post-crosslinking by treating with a Friedel-Crafts catalyst in a swollen state. Yet other of these polymers are a hypercrosslinked polystyrene produced from crosslinked styrene copolymers by an extensive additional post-crosslinking in a swollen state with bifunctional crosslinking agents selected from the group comprising of monochlorodimethyl ether and p-xylilene dichloride.

One preferred sorbent is Cytosorb™ marketed by Cytosorbents.

Some polymers useful in the practice of the invention are hydrophilic self-wetting polymers that can be administered as dry powder containing hydrophilic functional groups such as, amines, hydroxyl, sulfonate, and carboxyl groups.

Certain polymers useful in the invention are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex™ Optipore™ L-493, Dowex™ Optipore™ V-493, Dowex™ Optipore™ V-502, Dowex™ Optipore™ L-285, Dowex™ Optipore™ L-323, and Dowex™ Optipore™ V-503. Lanxess (formerly Bayer and Sybron): Lewatit™ VPOC 1064 MD PH, Lewatit™ VPOC 1163, Lewatit™ OC EP 63, Lewatit™ S 6328A, Lewatit™ OC 1066, and Lewatit™ 60/150 MIBK. Mitsubishi Chemical Corporation: Diaion™ HP 10, Diaion™ HP 20, Diaion™ HP 21, Diaion™ HP 30, Diaion™ HP 40, Diaion™ HP 50, Diaion™ SP70, Diaion™ SP 205, Diaion™ SP 206, Diaion™ SP 207, Diaion™ SP 700, Diaion™ SP 800, Diaion™ SP 825, Diaion™ SP 850, Diaion™ SP 875, Diaion™ HP 1MG, Diaion™ HP 2MG, Diaion™ CHP 55A, Diaion™ CHP 55Y, Diaion™ CHP 20A, Diaion™ CHP 20Y, Diaion™ CHP 2MGY, Diaion™ CHP 20P, Diaion™ HP 20SS, Diaion™ SP 20SS, and Diaion™ SP 207SS. Purolite Company: Purosorb™ AP 250 and Purosorb™ AP 400.

The present invention does not rely on charge or a ligand-receptor complex binding reaction to inhibit or reduce pathogen toxicity. A polymer using acid functional group(s) attached to the polymer backbone to bind *Clostridium difficile* Toxin A and Toxin B is described by Bacon Kurtz et al. (U.S. Pat. No. 6,890,523). The interaction in Kurtz is ionic where a hydrophobic or hydrophilic group attached to the polymer binds the toxin. Chamot et al. (US Patent Application 2006/009169) describe using inorganic polymer particles linked to a toxin binding moiety comprised of oligosaccharide sequences that bind *C. difficile* Toxin A and Toxin B. Also described is a toxin binding surface pore size 2× larger than toxin diameter. Chamot described oligosaccharide moieties that bind toxins to form a ligand/receptor-like complex.

The polymer materials used as the sorbent are generally not metabolizable by human and animal, but may be synthesized from materials characterized as being a biodegradable polymer, a resorbable polymer, or both. Certain polymers may be irregular or regular shaped particulates such as powders, beads, or other forms with a diameter in the range of 0.1 micron meters to 2 centimeters.

The polymers used in the instant invention preferably have a biocompatible and hemocompatible exterior surface coatings but are not absolutely necessary, especially in certain circumstances, such as oral or rectal administration. Certain of these coatings are covalently bound to the polymer particle (beads, for example) by free-radical grafting. The free-radical grafting may occur, for example, during the transformation of the monomer droplets into polymer beads. The dispersant coating and stabilizing the monomer droplets becomes covalently bound to the droplet surface as the monomers within the droplets polymerize and are converted into polymer. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

Porogens that may be used in the invention may be one or more of benzyl alcohol, cyclohexane, cyclohexanol, cyclohexanol/toluene mixtures, cyclohexanone, decane, decane/toluene mixtures, di-2-ethylhexylphosphoric acid, di-2-ethylhexyl phthalate, 2-ethyl-1-hexanoic acid, 2-ethyl-1-hexanol, 2-ethyl-1-hexanol/n-heptane mixtures, 2-ethyl-1-hexanol/toluene mixtures, isoamyl alcohol, n-heptane, n-heptane/ethylacetate, n-heptane/isoamyl acetate, n-heptane/tetraline mixtures, n-heptane/toluene mixtures, n-hexane/toluene mixtures, pentanol, poly(styrene-co-methyl methacrylate)/dibutyl phthalate, polystyrene/2-ethyl-1-hexanol mixtures, polystyrene/dibutyl phthalate, polystyrene/n-hexane mixtures, polystyrene/toluene mixtures, toluene, tri-n-butylphosphate, 1,2,3-trichloropropane/2-ethyl-1-hexanol mixtures, 2,2,4-trimethyl pentane (isooctane), trimethyl pentane/toluene mixtures, poly(propylene glycol)/toluene mixtures poly(propylene glycol)/cyclohexanol mixtures, and poly(propylene glycol)/2-ethyl-1-hexanol mixtures.

The present biocompatible sorbent compositions are comprised of a plurality of pores. The biocompatible sorbents are designed to adsorb a broad range of toxins from less than 1 kDa to 1,000 kDa. While not intending to be bound by theory, it is believed the sorbent acts by sequestering molecules of a predetermined molecular weight within the pores. The size of a molecule that can be adsorbed by the polymer will increase as the pore size of the polymer increases. Conversely, as the pore size is increased beyond the optimum pore size for adsorption of a given molecule, adsorption of the protein may or will decrease.

In one embodiment a porous polymer that absorbs small to midsize protein molecules equal to or less than 50,000 Daltons (50 kDa) and excludes absorption of large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 100 Å to 1,000 Å (pore diameter) of the sorbent is smaller than 3:1.

In another embodiment a porous polymer that optimally absorbs midsize to large size protein molecules of approximately 300,000 Daltons and excludes or minimizes absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 1,000 Å to 10,000 Å (pore diameter) of the sorbent is smaller than 2:1.

In another embodiment a porous polymer that optimally absorbs very large size protein molecules equal to or less than 1,000,000 Daltons and excludes or minimizes absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 10,000 Å to 40,000 Å (pore diameter) of the sorbent is smaller than 3:1.

Treatments

Degenerative diseases as well as aging are believed to mainly be based on a life-long accumulation of molecular damages within molecules, cells and tissues. An important example of damaging structures are the advanced glycation end products (AGEs). It is believed that AGEs may be related to many degenerative diseases. Illustrative degenerative disease are Alzheimer's disease, macular degeneration, osteoarthritis, atherosclerosis, heart disease and kidney failure. The instant methods and sorbents may be useful in treatment of the disease or may be used prophylactically.

The sorbent may be contained in a cartridge and the bodily fluid treated ex vivo. For example, blood or other bodily fluid is pumped out of the body, directly through a CytoSorb™ hemoperfusion cartridge where the beads remove AGEs, and the purified fluid is then pumped back into the body.

In some embodiments, the bodily fluid comprises saliva, nasopharyngeal fluid, blood, plasma, serum, saliva, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid, extracellular fluid, lymph, mucus, or vitreous humor.

In other embodiments, the treatment may be in vivo. For example, the compositions may be given orally, rectally or via a feeding tube. The sorbent can be supplied as a dry powder or other dry particulate capable of being wetted externally or internally in the alimentary canal, including in the gastric or enteric environment, with or without the addition of wetting agents such as ethyl or isopropyl alcohol, potable liquids such as water, or other carrier fluid. Other possible routes of administration include subcutaneous or transdermal delivery. In some embodiments, administration is topical. Such methods include ophthalmic administration, administration to skin or wounds, direct administration into a body cavity or joint, and delivery to mucous membranes such as nasal, oral, vaginal and rectal delivery or other delivery to the alimentary canal. In some embodiments, the treatment is extracorporeal. Extracorporeal administration would include removal of inflammatory mediators from blood or physiologic fluids by circulating the fluids through a device containing sorbent and returning it back to the body. In some embodiments, such methods include local or systemic administration through a parenteral route. Parenteral administration includes intravenous, intraarterial, subcutaneous, intraperitoneal or intramuscular injection or infusion; or intracranial (including intrathecal or intraventricular, administration).

The sorbent may be formulated as for example, a powder, a tablet, a capsule, a solution, a slurry, an emulsion, a suppository, or in a food substance. The sorbent may be packaged in portable bottles, vials, blister packs, bags, pouches, or other container that allows for either single or multiple dosages. Depending on the use, the sorbent may be sterile or non-sterile. The polymer may be sterilized by standard methods. Such methods are well known to those skilled in the art. The therapeutically effective amount can be administered in a series of doses separated by appropriate time intervals, such as hours. The compositions of the instant invention may be administered by methods well known to those skilled in the art.

EXAMPLES

The following examples are intended to be illustrative and non-limiting.

Example 1

Figure 1B:
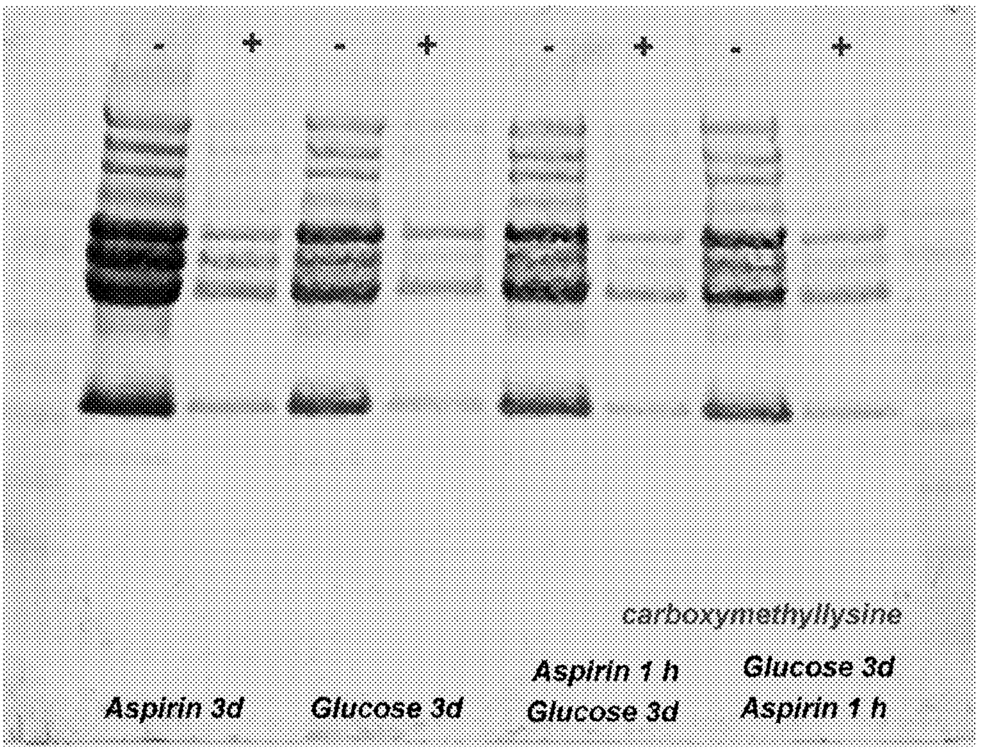
FIG. 1*b* shows that Cytosorbents Adsorber bind AGEs (CML) efficiently.

Plasma samples were treated with Aspirin/Glucose or both to induce posttranslational modifications. Samples were used directly (–) or after passage through a CytoSorbents adsorber (+), separated by gel electrophoresis, blotted and stained with antibodies against Acetyllysine or Carboxymethyllysine (CML, advanced glycation end product, AGE). FIG. 1*a* shows that Cytosorbents Adsorber does not bind Acetyllysine efficiently (comparison pairwise lanes (–/). FIG. 1*b* shows that Cytosorbents Adsorber does bind AGEs (CML) efficiently (comparison pairwise lanes (–/+)).

Example 2

Figure 2:
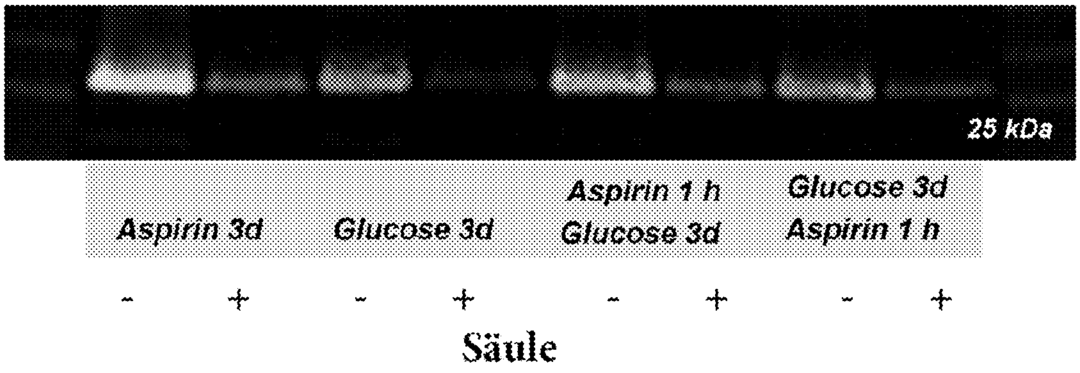
FIG. 2 shows concentration of 1 protein (25 kD): by staining CML green and Acetyllysine red (Odyssee system), it can be clearly seen that after a passage through an Cytosorbents adsorber, the green (GFP) modified proteins disappeared whereas red (Acetyllysine) modified proteins are still detectable.

This example utilizes a protein (25 kD) and stains CML green and Acetyllysine red (Odyssee system). In FIG. 2, it can be clearly seen that after a passage through an adsorber, the green (GFP) modified proteins disappeared whereas red (Acetyllysine) modified proteins are still detectable (comparison pairwise lanes (–/+)).

Example 3

It is observed that sorption of AGE molecules having a molecular weight of 80 or 100 or 120 kDa or more may be achieved by contacting bodily fluid with the instant sorbents.

What is claimed:

1. A method of treating a degenerative disease associated with advanced glycation end (AGE) products in a subject, the method comprising contacting a bodily fluid of the subject with an uncharged sorbent to reduce the concentration of the AGEs from the bodily fluid; wherein the uncharged sorbent comprises a plurality of pores ranging from 50 angstroms to 40,000 angstroms with a pore volume of 0.5 cc/g to 5.0 cc/g and a size of 0.05 mm to 2 cm; wherein the uncharged sorbent comprises at least one crosslinking agent, at least one monomer, at least one dispersing agent and at least one porogen, and wherein the at least one monomer is one or more of divinylbenzene and ethylvinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide, or mixtures thereof;

wherein the contacting occurs in vivo or the contacting occurs ex vivo and the bodily fluid is returned to the subject.

2. The method of claim 1, wherein the sorbent is biocompatible.

3. The method of claim 1, wherein the bodily fluid comprises saliva, nasopharyngeal fluid, blood, plasma, serum, saliva, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid, extracellular fluid, lymph, mucus, or vitreous humor.

4. The method of claim 1, wherein the sorbent has a pore structure such that the total pore volume of pore size in the range of 50 Å to 40,000 Å is greater than 0.5 cc/g to 5.0 cc/g dry sorbent; wherein the ratio of pore volume of pores having a diameter of between 50 angstroms to 40,000 angstroms to pore volume of pores having a diameter of between 1,000 angstroms to 10,000 angstroms of the sorbent is smaller than 2:1.

5. The method of claim 1, wherein the sorbent comprises at least one crosslinking agent and at least one monomer.

6. The method of claim 1, wherein the at least one dispersing agent is one or more of hydroxyethyl cellulose, hydroxypropyl cellulose, poly (hydroxyethyl methacrylate), poly (hydroxyethyl acrylate), poly (hydroxypropyl methacrylate), poly (hydroxypropyl acrylate), poly (dimethylaminoethyl methacrylate), poly (dimethylaminoethyl acrylate), poly (diethylamimoethyl methacrylate), poly (diethylaminoethyl acrylate), poly (vinyl alcohol), poly (N-vinylpyrrolidinone), salts of poly (methacrylic acid), or salts of poly(acrylic acid).

7. The method of claim 1, wherein the at least one crosslinking agent is one or more of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, or divinylformamide.

8. The method of claim 1, wherein the at least one porogen is one or more of benzyl alcohol, cyclohexane, cyclohexanol, cyclohexanol/toluene mixtures, cyclohexanone, decane, decane/toluene mixtures, di-2-ethylhexylphosphoric acid, di-2-ethylhexyl phthalate, 2-ethyl-1-hexanoic acid, 2-ethyl-1-hexanol, 2-ethyl-1-hexanol/n-heptane mixtures, 2-ethyl-1-hexanol/toluene mixtures, isoamyl alcohol, n-heptane, n-heptane/ethylacetate, n-heptane/isoamyl acetate, n-heptane/tetraline mixtures, n-heptane/toluene mixtures, n-hexane/toluene mixtures, pentanol, poly(styrene-co-methyl methacrylate)/dibutyl phthalate, polystyrene/2-ethyl-1-hexanol mixtures, polystyrene/dibutyl phthalate, polystyrene/n-hexane mixtures, polystyrene/toluene mixtures, toluene, tri-n-butylphosphate, 1,2,3-trichloropropane/2-ethyl-1-hexanol mixtures, 2,2,4-trimethyl pentane (isooctane), trimethyl pentane/toluene mixtures, poly(propylene glycol)/toluene mixtures poly(propylene glycol)/cyclohexanol mixtures, or poly(propylene glycol)/2-ethyl-1-hexanol mixtures.

9. The method of claim 1 wherein the contacting occurs ex vivo.

10. The method of claim 1 wherein the contacting occurs in vivo.

11. The method treatment of claim 1, wherein the degenerative disease is Alzheimer's disease.

12. The method treatment of claim 1, wherein the degenerative disease is a macular degeneration.

13. The method treatment of claim 1, wherein the degenerative disease is osteoarthritis.

14. The method treatment of claim 1, wherein the degenerative disease is atherosclerosis.

15. The method treatment of claim 1, wherein the degenerative disease is heart disease.

16. The method of claim 1, wherein the degenerative disease is kidney failure.

17. The method of claim 1, wherein the bodily fluid comprises blood and the contacting occurs ex vivo.

* * * * *